(12) United States Patent
Park et al.

(10) Patent No.: US 8,551,537 B2
(45) Date of Patent: Oct. 8, 2013

(54) RHUS VERNICIFLUA STOKES EXTRACT HAVING INCREASED CONTENT OF ACTIVE FLAVONOID COMPOUND AND METHOD FOR PREPARING SAME

(75) Inventors: Sang-Jae Park, Gyeonggi-do (KR); Kyung-Hee Kim, Gangwon-do (KR); Myung-Jae Shin, Gangwon-do (KR); Sang-Seok Lee, Gangwon-do (KR); Byung-Sik Kang, Gangwon-do (KR); Won-Cheol Choi, Incheon-si (KR); Sung-Pil Kwon, Seoul (KR)

(73) Assignee: AZI Company Ltd. (KR)

( * ) Notice: Subject to any disclaimer, the term of this patent is extended or adjusted under 35 U.S.C. 154(b) by 0 days.

(21) Appl. No.: 13/519,548

(22) PCT Filed: Dec. 27, 2010

(86) PCT No.: PCT/KR2010/009375
§ 371 (c)(1),
(2), (4) Date: Jun. 27, 2012

(87) PCT Pub. No.: WO2012/020892
PCT Pub. Date: Feb. 16, 2012

(65) Prior Publication Data
US 2012/0283322 A1    Nov. 8, 2012

(30) Foreign Application Priority Data
Aug. 11, 2010  (KR) .................. 10-2010-0077410

(51) Int. Cl.
*A01N 65/00*  (2009.01)
(52) U.S. Cl.
USPC ........................................................ 424/725
(58) Field of Classification Search
None
See application file for complete search history.

(56) References Cited

FOREIGN PATENT DOCUMENTS

| KR | 1020090048421 | 5/2003 |
| KR | 1020040027794 | 4/2004 |
| KR | 1020050047339 | 5/2005 |
| KR | 1020050107352 | 11/2005 |

OTHER PUBLICATIONS

Kim, Myong Jo., et al., "Anticancer and Antioxidant Activity of Allergen-Removed Extract in *Rhus verniciflua* Stokes," *Korean J. Medicinal Crop. Sci.*, 10(4): 288-293 (2002).

*Primary Examiner* — Michael Meller
(74) *Attorney, Agent, or Firm* — Sunstein Kann Murphy & Timbers LLP

(57) ABSTRACT

The present invention relates to *Rhus verniciflua* Stokes extract having an increased content of an active flavonoid compound through a gas bubbling treatment, a method for preparing the *Rhus verniciflua* Stokes extract, and a method for converting fustin into fisetin through the gas bubbling treatment of a solution containing fustin. The method for preparing the *Rhus verniciflua* Stokes extract of the present invention can convert the conventional *Rhus verniciflua* Stokes extract having high content of fustin and low content of fisetin into a *Rhus verniciflua* Stokes extract having high content of fisetin. Therefore, the *Rhus verniciflua* Stokes extract of the present invention can be commercialized into natural anticancer agents, anticancer and cancer prevention food products, and health functional foods due to the excellent bioactivity thereof, and promote the development of relevant industries through the high added-value of *Rhus verniciflua* Stokes. In addition, the method for converting fustin into fisetin can be applied to other natural substances and be used as a method for enhancing the functionality thereof by increasing the content of a high active flavonoid, thereby becoming an enabling technology that can lead high-functionalization of natural substances.

4 Claims, 1 Drawing Sheet

RHUS VERNICIFLUA STOKES EXTRACT HAVING INCREASED CONTENT OF ACTIVE FLAVONOID COMPOUND AND METHOD FOR PREPARING SAME

CROSS-REFERENCE TO RELATED APPLICATION

This application is a national phase entry of international patent application no. PCT/KR2010/009375 filed Dec. 27, 2010 and claims the benefit of Korean patent application No. 2010-0077410, filed Aug. 11, 2010, the disclosures of which are incorporated herein by reference in its entirety.

BACKGROUND

1. Field of the Invention

The present invention relates to a method for preparing a *Rhus verniciflua* stokes extract having an increased content of an active flavonoid compound by performing a gas bubbling treatment on the *Rhus verniciflua* stokes extract; the *Rhus verniciflua* stokes extract prepared by the above method; and a method of converting fustin into fisetin by performing a gas bubbling treatment on a solution containing fustin.

2. Discussion of Related Art

*Rhus verniciflua* stokes is fallen leaves broad leaf arborescent belonging to the Anacardiaceae family and it is known that *Rhus verniciflua* stokes is originally from the Himalayas and highlands of Central Asia. It is now distributed widely throughout the world, from the subtropics to the temperate regions, with the tropics as the center. *Rhus verniciflua* stokes is fallen leaves or evergreen trees and most of them are shrub trees or tall trees, but some of them are climbing trees (Barkley Fred Alexander., Ann. of the Missouri Bot. Garden., 24(3), pp 265-500, 1937).

A sap of *Rhus verniciflua* stokes is known as an oriental lacquer. In terms of oriental medicine, it is widely known that a dried oriental lacquer removes extravasated blood; improves blood circulation; and is effective in reducing or alleviating hookworm, stomachache, excessive acid in the stomach, thick sputum, tuberculosis, period pains, constipation, diabetes, malaria, anti-inflammatory, arthritis, and is useful for use as a preservative, strengthening the stomach, easing menstruation pain, and the like, and it is recently known that it is effective in preventing cancer (Namba, T., Colored Illustrations of Wakan Yaku. p 215, Hoikusha Publishing Co. Ltd., Osaka, 1980). In addition, in terms of common medicine, it is known that it is useful as a digestive medicine; it controls extravasated blood in the liver; it controls cardiac disease as a drug for cleaning blood in the heart; removes tuberculosis germs in the lung; and also it is an excellent drug for neuralgia, arthritis, skin diseases, and the like because *Rhus verniciflua* stokes and a wild ginseng are comparable to each other in effect.

It is already known from much research that *Rhus verniciflua* stokes include a lot of anti-oxidative substances. Specifically, it is known that the *Rhus verniciflua* stokes extract that is extracted by using ethanol has strong anti-oxidative activity and also the fraction that is isolated and purified by using a silica column has an ability for inhibiting the growth of tumor cells in the human blood. In addition, it is also known that a substance having an antimicrobial effect is isolated from the *Rhus verniciflua* stokes extract that is extracted by using ethanol and *Rhus verniciflua* stokes skin extract that is extracted by using methanol has various bioactivity effects related to the *Rhus verniciflua* stokes extract, such as an effect on suppressing obesity.

Compounds that are found in *Rhus verniciflua* stokes genus until now include fisetin, fustin, agathisflavone, eicosanedioic acid, europetein, butein, corilagin, 3'4'-dihydroxy-flavone, lantabetulic acid, myricetin, syringin, semialatic acid, palasitrin, sulfuretin, 3-pentadecyl-1,2-benzenediol, demethoxykanugin, ovalitenone, semimornic acid, 2-(3, 4-dihydroxybenzyl)-2,6-dihydroxy-3(2H)-benzofuranone, mesuaferrone A, resokaempferol, rhoifolin, rhusflavanone, succedaneaflavanone, fisetin; 7-0-β-D-glucopyranoside, bhilawanol, tannin, hydrolaccol, stellacyanin, quercetin, cynarine, and the like, and the largest content of the components among them is fustin.

The above components are mostly flavonoid-based materials and flavonoids, such as fisetin and fustin, which play a role in protecting blood vessels or capillaries. And also, the fisetin and fustin are very excellent bioactive substances having antioxidative activity, anti-inflammatory properties, and anticancer properties. However, the fustin that is plentifully included in the *Rhus verniciflua* stokes extract has a disadvantage wherein its activity is greatly decreased as compared to the activity of fisetin in terms of bioactivity. On the other hand, the fisetin has activitystrong anticancer activity so that it is now being used as an anticancer drug, but there is a disadvantage that a major component of most conventional *Rhus verniciflua* stokes extracts is the fustin and the fisetin is included in small quantity as compared to the fustin.

Accordingly, when the *Rhus verniciflua* stokes extract containing a lot of fisetin with excellent bioactivity may be prepared, the *Rhus verniciflua* stokes extract may have relatively excellent anticancer activity and bioactivity so that it can be expected to be very useful in the food and medicine industries.

SUMMARY OF THE INVENTION

Accordingly, the present inventors preformed research into a method for preparing a *Rhus verniciflua* stokes extract having very excellent bioactivity by controlling the content of a flavonoid compound in the *Rhus verniciflua* stokes extract.

Therefore, the present inventors completed the present invention by developing a method for preparing new *Rhus verniciflua* stokes extract including a large quantity of fisetin having various bioactivities, as well as anti-oxidative activities and anticancer activities.

Accordingly, it is an object of the present invention to provide *Rhus verniciflua* stokes extract with an increased content of an active flavonoid compound by converting fustin, a flavonoid compound, into fisetin, an active flavonoid compound, in which the active flavonoid compound is plentifully included in the *Rhus verniciflua* stokes extract.

In order to achieve the above objects, there is provided a method for preparing a *Rhus verniciflua* stokes extract with an increased content of an active flavonoid compound, including: extracting *Rhus verniciflua* stokes extract using an extraction solvent; and performing a gas bubbling treatment into the *Rhus verniciflua* stokes extract.

In an embodiment of the present invention, the gas may include oxygen.

In an embodiment of the present invention, the gas bubbling treatment may be performed by using at least one way of implementation thereof along with the extraction of *Rhus verniciflua* stokes at the same time, or after completing the extraction of *Rhus verniciflua* stokes. Preferably, the gas bubbling treatment may be performed by at least one method of directly bubbling gas through the extract solution inside an extractor, or contacting gas with the extract solution outside the extractor.

In an embodiment of the present invention, the active flavonoid is fisetin.

In an embodiment of the present invention, the *Rhus verniciflua* stokes extract may be extracted by at least one solvent for extracting selected from the group consisting of water, alcoholic solvent, methanol, ethanol, propanol, isopropanol, butanol, acetone, ether, benzene, chloroform, ethylacetate, methylenechloride, n-hexane, hydrochloric acid, acetic acid, formic acid, citric acid, cyclohexane, and combination thereof.

In an embodiment of the present invention, the gas may be air and the time for the gas bubbling treatment may be 6 to 24 hours. Preferably, the time for the gas bubbling treatment may be 8 to 12 hours.

In an embodiment of the present invention, the gas may be oxygen with high purity, preferably at least 95% (v/v), and more preferably pure oxygen, and the time for the gas bubbling treatment may be 5 to 12 hours. Preferably, the time for the gas bubbling treatment may be 7 to 10 hours.

In addition, the present invention provides a *Rhus verniciflua* stokes extract including fisetin prepared by performing a gas bubbling treatment, wherein the content ratio of fisetin:fustin in the extract is 1:0 to 2:1. This means that the content ratio value of fisetin/fustin is 2 or more.

In addition, the present invention provides a method of converting fustin into fisetin, including performing a gas bubbling treatment into a solution containing fustin.

In an embodiment of the present invention, the gas may be air and the time for the gas bubbling treatment may be 6 to 24 hours. Preferably, the time for the gas bubbling treatment may be 8 to 12 hours.

In an embodiment of the present invention, the gas may be oxygen with high purity, preferably at least 95% (v/v), and more preferably pure oxygen, and the time for the gas bubbling treatment may be 5 to 12 hours. Preferably, the time for the gas bubbling treatment may be 7 to 10 hours.

In addition, the present invention provides a *Rhus verniciflua* stokes extract including fisetin, wherein the content ratio of fisetin:fustin is 1:0 to 2:1.

In addition, the present invention provides a pharmaceutical composition including the *Rhus verniciflua* stokes extract as an effective component for preventing or treating cancer.

In addition, the present invention provides a health functional food including the *Rhus verniciflua* stokes extract as an effective component for preventing cancer or improving cancer symptoms.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
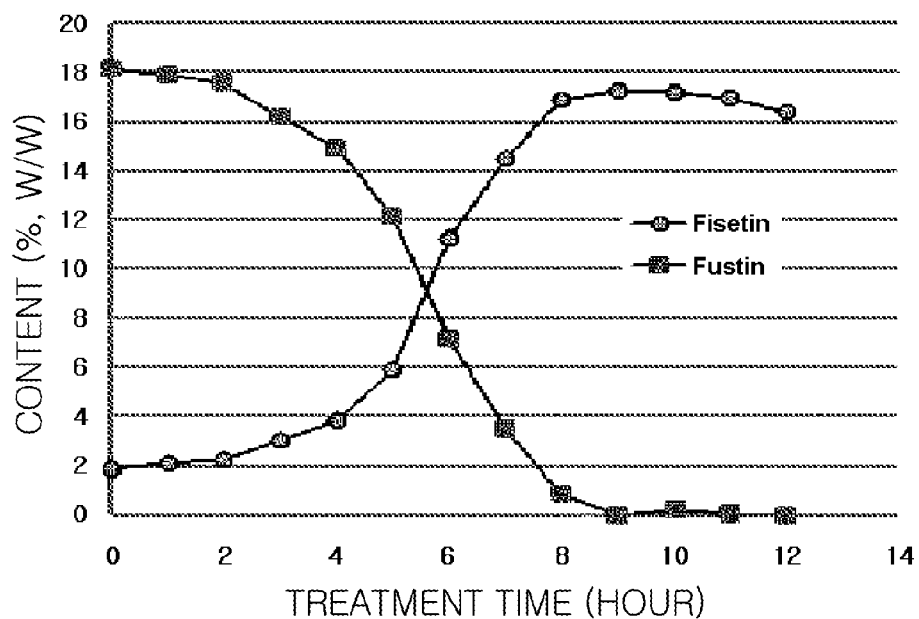
FIG. 1 is a graph showing an effect on converting fustin into fisetin according to time when air bubbling treatment is applied to *Rhus verniciflua* stokes extract.

The present invention provides a method for preparing a *Rhus verniciflua* stokes extract having an increased content of an active flavonoid compound, including extracting *Rhus verniciflua* stokes extract using an extraction solvent; and performing a gas bubbling treatment into the *Rhus verniciflua* stokes extract.

*Rhus verniciflua* stokes is known as a fallen leaves broad leaf arborescent belonging to the Anacardiaceae family; it is spread throughout subtropical zones and tropical regions; and 60 genus and 400 species trees belong to *Rhus verniciflua* stokes all over the world. It is known that one of active flavonoids that are included in *Rhus verniciflua* stokes extract, fisetin (2-(3,4-dihydroxyphenyl)-3,7-dihydroxy-4H-chromen-4-one-hydrate, 3,3',4',7'-tetrahydroxyflavone) has an excellent effect in a wide variety of fields, as follows: anticancer activities (Haddad A Q et. al., Nutr. Cancer, 2010, 62(5), 668-81), anti-dementia activities (Zheng L T et. al., Int. Immunopharmacol., 2008, 8(3), 484-94), memory improvement (Maher P. et. al., PNAS, 2006, 103(44), 16568-73), an improvement of symptoms of arthritis (Lee J D et. al., Int. Immunopharmacol., 2009, 9(3), 268-76), anti-inflammatory activities (Geraets L. et. al., Biochem. Biophys Res Commun. 2009, 382(3), 598-603), an improvement of blood circulation (Park Y H et. al., J. Ocul Pharmacol. Ther., 2004, 20(3), 189-200), and the like.

In *Rhus verniciflua* stokes, the content of flavonoid component that is known as a medical component is increased with tree age. Generally, only when the tree age is over 10 years, the content of flavonoid may be included in about 15 to 20% (w/w) among the extract based on the extract. 13 to 17% (w/w) among them is fustin (2,3-Dihydrofisetin) represented by Chemical Formula 1, 1 to 3% (w/w) is fisetin represented by Chemical Formula 2, and then trace amounts of sulfuretin, butein, and the like are included.

[Chemical Formula 1]

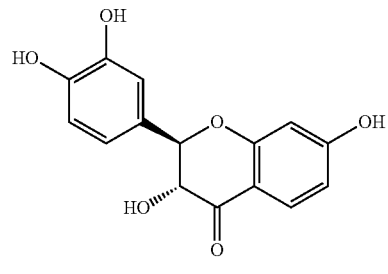

Fustin (2,3-Dihydrofisetin)

[Chemical Formula 2]

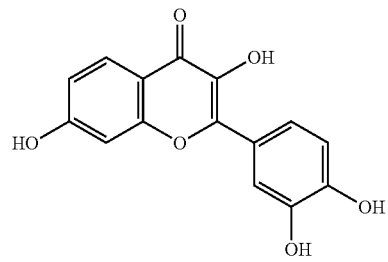

Fisetin
(3,3',4',7'-tetrahydroxyflavone)

It is known that fustin that is plentifully included in *Rhus verniciflua* stokes extract has antioxidative activity, anticancer activity, etc. like fisetin, but useful bioactivity of fustin is greatly decreased as compared to that of fisetin. The comparison experiment for antioxidative activities between fustin and fisetin that was confirmed by the present inventors supports the above fact (see Table 1). That is, according to an embodiment of the present invention, it has been seen that the anti-oxidative activity of fisetin was excellent by at least 5 times as compared with that of fustin as a result of the comparison experiment for anti-oxidative activities between fustin and fisetin.

TABLE 1

| Substance | Anti-oxidative Activity ($IC_{50}$, ug/ml) |
|---|---|
| Fustin | 33 |
| Fisetin | 8 |

Accordingly, since fustin has relatively low bioactivity effect as compared with that of fisetin that is an active flavonoid having excellent anticancer and anti-oxidative activities, fustin refers to a "non-active flavonoid" for the present invention.

Therefore, the present invention provides a method for preparing a Rhus verniciflua stokes extract by converting fustin that is plentifully included in Rhus verniciflua stokes extract into fisetin that is an active flavonoid with excellent bioactivity, and the Rhus verniciflua stokes extract prepared according to the present invention includes a large quantity of an active flavonoid compound.

The method for preparing the Rhus verniciflua stokes extract according to the present invention includes performing a gas bubbling treatment on Rhus verniciflua stokes extract.

The Rhus verniciflua stokes refers to the trees belonging to the Anacardiaceae family, and a type of useable Rhus verniciflua stokes may include any one or more selected from the group consisting of Rhus trichocarpa MIQ, Rhus verniciflua, Rhus cotinus, Rhus ambigua H.Lev., Succedanea Sumac, and Rhus succedanea L., but the present invention is not limited thereto. Preferably, Rhus verniciflua may be used.

A proper solvent for extracting Rhus verniciflua stokes extract according to the present invention may include water and an organic solvent, and preferably may include alone or a combination of various solvents, such as water, alcoholic solvent, methanol, ethanol, propanol, isopropanol, butanol, acetone, ether, benzene, chloroform, ethylacetate, methylenechloride, n-hexane, hydrochloric acid, acetic acid, formic acid, citric acid, cyclohexane, petroleum ether, and the like. More preferably, water, an alcoholic solvent, and methanol may be used, and most preferably, water may be used.

The Rhus verniciflua stokes extract according to the present invention may be prepared by a general method for preparing an extract, and specifically, may be prepared by a hot-water extraction method, a macerating extraction method, a digesting extraction method, and the like, and may be prepared by using a general extracting machine, sonicator, or fractionators. In addition, the extract is extracted by using a solvent and then filtering, concentrating, or drying may be selectively performed to remove the solvent from the extract or all of filtering, concentrating, and drying may be performed to remove the solvent from the extract. Specifically, the filtering may include decompression filtering or pressurization filtering using a filter for filtering, and the concentrating may include decompression concentrating in a vacuum. In addition, water of the resulting extract may be completely removed through the concentrating and drying, and the Rhus verniciflua stokes extract without water may be used in a type of powder or the powder may be solved in distilled water or general solvent to use. Accordingly, the Rhus verniciflua stokes extract including a high content of an active flavonoid compound that is obtained by extracting and converting the Rhus verniciflua stokes extract according to the present invention may be commercialized as an extract powder or extract solution through filtering, concentrating, or drying process.

In addition, useable gas in the bubbling treatment may include gas containing oxygen, if it does not disrupt the reaction, preferably, high purity oxygen, and more preferably, pure oxygen, but the present invention is not limited thereto.

A method for preparing the Rhus verniciflua stokes extract with an increased content of an active flavonoid compound according to the present invention are described in more detail, as follows:

Water, alcoholic solvent, an organic solvent, or diluents solution thereof is added as a solvent for extracting Rhus verniciflua stokes, and then is heated to extract. In the extracting process, gas, preferably the gas containing oxygen is bubbled through the extraction solution or concentration solution. The above process is performed to convert fustin, a non-active flavonoid compound into fisetin, active flavonoid, in which the fustin is plentifully included in the extract extracted from Rhus verniciflua stokes. The gas bubbling process may be performed with extracting at the same time, after extracting for a certain time, or after making the concentration solution through the concentrating of the extraction solution that is completely extracted.

The bubbling gas may include a gas containing oxygen, preferably, air or high purity air, and preferably, pure oxygen. When the purity degree of oxygen is high, it has an advantage that even though the processing time is short; the same effect can be obtained. The purity of oxygen included in the bubbling gas is 20% (v/v) in the case of air. According to a method of supplying high purity oxygen with at least 95% (v/v) purity, the higher the purity of oxygen, the shorter the time required for converting fustin into fisetin; and the lower the purity of oxygen, the longer the time required thereby requiring a considerable time for completely converting.

When the bubbling treatment is performed for a short time, less than 1 hour, fustin is only slightly or very slightly converted into fisetin so that there is a Lag-time, in which the components are not changed for a period of time, such that a proper gas bubbling treatment time is required. On the other hand, excessive oxygen bubbling causes decomposition after converting fustin into fisetin so that it is important that a proper time should be selected.

A case of applying the similar method as the method of the present invention to remove an allergy inducing material is disclosed in Korean Patent No. 10-0918326, but there is no technology for converting fustin into fisetin with high activity. The removal of an allergy inducing material is performed along with a supply of oxygen at the same time and completed within a short time, while the conversion of fustin into fisetin is gradually preformed at the end of completing the removal of the allergy inducing material. Accordingly, the conversion of fustin into fisetin may be a new technological idea that is not disclosed or has not been invented in the conventional art for a processing condition thereof.

When the gas for bubbling is air, it is preferable that the air bubbling treatment is continuously maintained for 6 to 24 hours, and more preferably for 8 to 12 hours in order to prepare Rhus verniciflua stokes extract with an increased content of an active flavonoid compound according to the present invention.

In addition, when the gas for bubbling is high purity oxygen, it is preferable that the bubbling treatment is continuously maintained for 5 to 12 hours, and more preferably for 7 to 10 hours in order to prepare *Rhus verniciflua* stokes extract with an increased content of an active flavonoid compound according to the present invention.

The amount and time for bubbling oxygen may be generally based on volumetric flow rate (l/min) of gas, and preferably, unit volumetric flow rate (VVM, l/min/volume) which is the volumetric flow rate divided by a volume of solution. The time for supplying of air may be 1 to 40 hours depending on a gas supplying flow. However, when the time passes 12 hours, most of fustin is converted into fisetin, such that further supplying of air is not substantially need. Of course, when the supply rate of gas is very slow, the time for completely converting into fisetin may require at least 20 hours. Accordingly, the conversion rate of fustin into fisetin may be possibly controlled by changing a flow rate of gas or the time for supplying gas.

Therefore, the present invention may provide *Rhus verniciflua* stokes extract with an increased content of an active flavonoid compound due to the gas bubbling treatment, and also provide *Rhus verniciflua* stokes extract, in which 45 to 100% of the conventional content of fustin presented in *Rhus verniciflua* stokes extract may be converted into fisetin. That is, all of fustin that is an essential component of the conventional *Rhus verniciflua* stokes extract can be substantially converted into fisetin through a method of extracting *Rhus verniciflua* stokes according to the present invention so that there may be substantially no fustin in the *Rhus verniciflua* stokes extract according to the present invention.

Therefore, the present invention may provide *Rhus verniciflua* stokes extract having the content ratio of 1:0 to 2:1 of fisetin:fustin.

The bubbling condition of gas through *Rhus verniciflua* stokes extract is varied according to the pressure or purity of the used gas. That is, in relation to the pressure, the bubbling may be continuously performed on the bottom of an extractor through a blower, etc. under atmospheric pressure, or may be performed by supplying high-pressure gas. It may not be affected by the internal pressure of the extractor. That is, even when the internal pressure of the extractor or concentrator is maintained within a range of 0 to 10 atmospheric pressures, the effect may not be changed. The greater the pressure, the greater the solubility of oxygen is increased so that the processing time may be reduced, but economic feasibility and stability may be significantly reduced due to a sharp increase of installation cost in order to maintain high pressure.

For a method for preparing a *Rhus verniciflua* stokes extract according to the present invention, the gas bubbling may be generally disclosed in the case of supplying at the bottom of the extractor, but may be performed by using a way of supplying gas through an appropriate pipe after installing the appropriate pipe inside the extractor. Also, the gas bubbling may be performed by a way of separately supplying a gas to allow for contact between the extract solution and the bubbling gas outside the extractor. Here, it may be a general system of contacting liquid and gas, and the system may include a wider area that can allow for contact between the gas and extract solution as a separate space or in the upper of the extractor. Accordingly, the gas bubbling treatment according to the present invention may include a method of bubbling gas through the extract solution of *Rhus verniciflua* stokes inside the extractor that is used for extracting, a method of contacting the bubbling gas and the extract solution outside the extractor, a method of flowing the gas and extract solution in the same directions or reverse directions at the same time, or a method of using an apparatus, such as an inline mixer, as a machine for mixing the gas and extract solution.

The *Rhus verniciflua* stokes extract prepared by the method of the present invention may be reconstituted as a fractional material with a high content of fisetin through a further fractionation process. That is, when the solution fractionation may be performed by using acetone, ethyl acetate, n-butanol, chloroform, and the like, as organic solvent, the fractional material that is improved by 30 to 45% (w/w) of fisetin content may be prepared from the extract with 5 to 25% (w/w) of fisetin content. In addition, the purified material with at least 90% (w/w) purity of fisetin may be obtained by performing re-crystallization of the same. However, when the method for preparing a *Rhus verniciflua* stokes extract according to the present invention is not applied, the fisetin with high purity may not be easily obtained by fractionation and/or re-crystallization due to an interference of fustin even though the organic solvent is used. Accordingly, in case of performing the fractionation and/or re-crystallization according to the inventive conversion method, there is provided an effective way of obtaining plentiful amounts of high purity fisetin.

Generally, a method for preparing a *Rhus verniciflua* stokes extract may include adding water, alcoholic solvent, or diluted alcoholic solvent to *Rhus verniciflua* stokes, extracting the same, and then concentrating and/or drying the same. In this case, the composition of flavonoid in the *Rhus verniciflua* stokes extract may be composed of 10 to 30% (w/w) of fustin, 1 to 4% (w/w) of fisetin, and 0.1 to 2%(w/w) of other flavonoid content. In the case of flavonoid, the content is increased with tree age. The rate of fustin and fisetin in *Rhus verniciflua* stokes may be usually maintained within a constant range, and the whole content is increased with tree age. In this case, the content ratio of fisetin:fustin may be from the minimum 1:2.5 to the maximum 1:30, and generally 1:5 to 1:15.

Like this, the content ratio of fisetin:fustin may be generally in the range of 1:2.5 to 30. However, in the case of *Rhus verniciflua* stokes extract according to the inventive method for preparing a *Rhus verniciflua* stokes extract, the content ratio of fisetin:fustin may be adjusted low by less than 1:0.2. Generally, the difference of activities may be great since the content ratio of fisetin:fustin of 1:1, and it may preferably be 5:1, which means that the content of fisetin is 5 times the content of fustin and also the content of fisetin is significantly increased as compared with the conventional *Rhus verniciflua* stokes extract. In this case, the content of polyphenol that is known to have bioactivity, such as anti-oxidative activity, immunity-boosting properties, and the like is also very highly maintained at 40 to 70% (w/w).

When fustin is substantially and completely converted into fisetin by supplying high purity oxygen, the content ratio of fisetin:fustin may be maintained at a level of 1:0.001. It means that almost all of fustin is converted into fisetin and the *Rhus verniciflua* stokes extract with high content of fisetin obtained from the above process may become a *Rhus verniciflua* stokes extract having high bioactivity.

Accordingly, as compared with the conventional *Rhus verniciflua* stokes extract, the *Rhus verniciflua* stokes extract having an increased content of active flavonoid compounds according to the present invention may have excellent bioactivities, such as anticancer activity, anti-dementia activity, an improvement of memory, an improvement of arthritis, anti-inflammatory activity, anti-oxidative activity, an improvement of blood circulation, and the like.

According to an embodiment of the present invention, as compared with the conventional *Rhus verniciflua* stokes extract, it has been seen that the *Rhus verniciflua* stokes extract prepared through the inventive preparation method has very excellent anticancer and anti-oxidative activities (see Examples 3 and 4). Especially, with reference to the anticancer activity of the *Rhus verniciflua* stokes extract according to the present invention, according to an embodiment of the present invention, it has been seen as a result of comparing the effects on inhibiting growth of cancer cells in mice injected with of the conventional *Rhus verniciflua* stokes extract and the *Rhus verniciflua* stokes extract of the present invention that the weight and volume of cancer in the mice injected with the *Rhus verniciflua* stokes extract having a large quantity of fisetin according to the present invention are significantly decreased as compared with the mice injected with the conventional *Rhus verniciflua* stokes extract (see Table 3). The above result supports the reported excellent anticancer activity of the *Rhus verniciflua* stokes extract according to the present invention having a large quantity of fisetin that is known to have excellent anticancer activity.

Therefore, the present invention may provide an anticancer composition including the *Rhus verniciflua* stokes extract with the content ratio of fisetin:fustin of 1:0 to 2:1 as an effective component, and the composition according to the present invention may be used for treating and preventing cancer as a pharmaceutical composition. In addition, the anticancer composition according to the present invention may include 0.1 wt % to 100 wt % of the *Rhus verniciflua* stokes extract based on total weight of the composition.

A type of cancer that can be treated with the composition according to the present invention may be liver cancer, stomach cancer, colorectal cancer, lung cancer, breast cancer, rectal cancer, leukemia, pancreatic cancer, and the like, but the present invention is not limited thereto.

The anticancer composition according to the present invention may include alone a pharmaceutically effective amount of the *Rhus verniciflua* stokes extract, or at least one of a pharmaceutically acceptable carrier, excipient, or diluents. The term "a pharmaceutically effective amount" refers to a sufficient amount for preventing, improving and/or treating cancer symptoms.

A pharmaceutically effective amount of the *Rhus verniciflua* stokes extract according to the present invention may be 0.5 to 100 mg/day/weight kg, and preferably 0.5 to 5 mg/day/weight kg. However, the pharmaceutically effective amount may be appropriately changed according to a degree of cancer symptoms, an age of patient, a weight of patient, a health condition of patient, a sex of patient, an administering route, a period of treatment, and the like.

The expression "pharmaceutically acceptable" refers that it may be physiologically acceptable, and a side effect or the similar effect thereof, such as a gastroenteric trouble, and dizziness, may not generally be caused when administering to humans. Examples of the carrier, excipient, and diluents may include lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methyl hydroxybenzoate, propyl hydroxybenzoate, talc, magnesium stearate, and minerals. In addition, they may further include a filler, anticoagulants, lubricant, wetting agent, flavoring, emulsifying agent, preservatives, and the like.

In addition, the composition of the present invention may be formulated by using a method that is known in the art in order to provide a rapid, continuous, or delayed release type of an active component after administering to a mammal. The dosage form may be a type of powder, granule, tablet, emulsion, syrup, aerosol, soft or hard gelatin capsule, a sterile injection solution, or a sterile powder.

The anticancer composition according to the present invention may be administered through various routes, such as oral, a percutaneous, a subcutaneous, an intravenous, or an intramuscular injection. The dosage of active component may be appropriately selected according to various factors, such as an administering route, an age, a sex, and a weight of patient, severity of patient, and the like. In addition, the anticancer composition of the present invention may be administered along with the compounds that are known to have an effect on preventing, improving, or treating cancer symptoms. Accordingly, the present invention may provide a medicine for preventing and/or treating cancer symptoms, in which the medicine includes the *Rhus verniciflua* stokes extract according to the present invention.

Moreover, the anticancer composition according to the present invention may provide an effect on relieving cancer symptoms through functions of excellent anticancer and anti-oxidative activities, and also since it may be added to food in order to prevent or improve cancer symptoms, the composition of the present invention may be used for food in order to prevent and improve cancer symptoms. Accordingly, the composition of the present invention may be useful in foods having effects on preventing and improving cancer symptoms, such as, main raw materials or added raw materials of foods, food additives, functional foods or beverages.

According to the present invention, the term "food" refers to a natural material or processed material that may include one or more nutrients, and preferably to be eaten after some processing. As a general meaning, it may refer that all of foods, food additives, functional foods, and beverages are included.

The foods that can include the anticancer composition according to the present invention may be, for example, all sorts of foods, beverages, gums, teas, vitamin complexes, functional foods, and the like. Additionally, the foods that may be used in the present invention may be special nutritious foods (for example, milk formulas, young children and baby food, etc.), processed meat food, fish meat food, bean curd food, muk (gel type food), noodles (for example, ramen, noodles, etc.), breads, dietary supplements, seasoning food (for example, soy sauce, Doenjang (Korean traditional sauce), red pepper paste, etc.), sauces, confectionery (for example, snacks), candy, chocolates, gums, ice creams, milk products (for example, fermented milk, cheese, etc.), other processing foods, Kimchi, salting foods (all sorts of Kimchis, Jangajjis, etc.), beverages (for example, fruit beverages, vegetable beverages, soybean milk, fermented drinks, etc.), natural seasoning (for example, ramen soups, etc.), and the like, but the present invention is not limited thereto. The above foods, beverages, or food additives may be prepared by using a general preparation method.

In addition, the term "functional food" refers to a food group of giving a high added value to food function and expresses a function of a relevant food for a particular purpose using physical, biochemistry, and/or biotechnology methods, and the like and also a processed food by designing for sufficiently expressing a body controlling function related to a body defense mechanism, prevention and recovery of disease, and the like, which are functions of food. Specifically, it may be a health functional food. The functional food may include a cytologically acceptable food supplement and may further include an appropriate carrier, excipient, and diluents that are generally used for preparing a functional food.

In addition, the term "beverage" refers to the generic term for drinking for quenching thirst or enjoying taste, and may include a functional beverage. The beverage may include a composition with the disclosed rate for preventing and improving anticancer symptoms as an essential component, and other components, without any special limitation, and also may include various flavouring agents, natural carbohydrates, and the like, as a further component, like the general beverage.

In addition to the above disclosed components, the food including the composition according to the present invention may include various nutritional supplements, vitamins, minerals (electrolyte), flavouring agents, such as synthetic flavouring agents, natural flavouring agents, and the like, colorings, fillers (cheese, chocolates, etc.), pectic acid and salts thereof, alginic acid and salt thereof, organic acid, protective colloid thickener, pH control agent, stabilizer, preservatives, glycerin, alcohol, carbonation agent that is used for a carbonated drink, and the like, and the above components may be used alone or in combination.

For the food including the anticancer composition of the present invention, the amount of the composition of the present invention may be included in 0.001 wt % to 100 wt %, and preferably, 0.1 wt % to 40 wt %. For the beverage, it may be included in the range of 0.001 g to 5 g, and preferably 0.01 g to 2 g based on 100 ml, but it may be below the above ranges when it is taken for a long time for improving health and hygiene, and for managing health. Since, an effective component has no problem in terms of stability, it may be used in the amount of the above ranges, and the present invention is not limited thereto.

Therefore, the present invention may provide a health functional food including the *Rhus verniciflua* stokes extract as an effective component according to the present invention for preventing cancer or improving cancer symptoms, and a type of the food may be powder, granule, tablet, capsule, or drink, but the present invention is not limited thereto.

On the other hand, a method for preparing a *Rhus verniciflua* stokes extract having an increased content of an active flavonoid compound according to the present invention may convert a non-active flavonoid compound having a relatively low bioactivity into an active flavonoid compound having excellent bioactivity as mentioned above. At this point, the non-active flavonoid compound may be fustin and the active flavonoid compound may be fisetin. Accordingly, the present invention may provide the method of converting fustin into fisetin.

The method of converting fustin into fisetin may include performing a gas bubbling treatment on a solution containing fustin and the gas bubbling treatment may be performed by bubbling gas through an extract solution inside the extractor or contacting bubbling gas with the extract solution outside the extractor. The solution containing fustin may be an extract extracted from a natural material; and it may be a solution or extract containing fustin and fisetin at the same time; or it may be a solution or extract containing fustin only.

In addition, when the gas for bubbling is air, preferably, the bubbling treatment may be continuously maintained for 6 to 24 hours and more preferably, for 8 to 12 hours in order to prepare the solution containing high content of fisetin through the method of converting fustin into fisetin according to the present invention.

On the other hand, when the gas for bubbling is high purity oxygen, preferably, the bubbling treatment may be continuously maintained for 5 to 12 hours and more preferably, for 7 to 10 hours in order to prepare the solution containing high content of fisetin through the method of converting fustin into fisetin according to the present invention.

Accordingly, the present invention may convert the extract or solution having a large quantity of fustin into the extract or solution having a large quantity of fisetin that is an active flavonoid compound with excellent bioactivity.

Hereinafter, the present invention will be described in more detail with reference to the following Examples.

However, the following Examples are only for illustrating the present invention, and the content of the present invention is not limited to the following Examples.

Example 1

Preparation of *Rhus Verniciflua* Stokes Extract Through Gas Bubbling

The contents of fustin and fisetin that are included in *Rhus verniciflua* stokes extract were analyzed using HPLC. The standard products were purchased from Sigma Aldrich. As conditions of analyzing by HPLC, UV of 254 nm was used as a detector and 5% mixing solution of acetic acid:methanol:acetonitrile=70:20:10 was used for a moving phase. Total of 10 ul was injected at the flow rate of 1 ml/min. $C_{18}$ (250 mm*4.6 mm, YMC Pack) was used as a column. An analysis of polyphenol was performed by using tannic acid as a standard material with Folin-ciocalteu's phenol reagent. An absorbance was measured at 725 nm after developing color, and calculated using an external calibration method with a standard material.

<1-1> Preparation of *Rhus Verniciflua* Stokes Extract Through Air Bubbling 100 l of water was added to 10 kg of *Rhus verniciflua* stokes and then extracted at 95° C. for 6 hours. When a large quantity of flavonoid component was included in the extract after 4 hours during extraction, air (rate of oxygen: 20% (v/v)) was bubbled at the bottom of the extractor at the rate of 1.5 l/min. The time for bubbling was totally 12 hours and the components were analyzed by collecting a sample every hour.

As a result, the content of fustin was significantly decreased as time passes and the content of fisetin was increased (FIG. 1). After 11.5 hours, substantially 100% of fustin was converted into fisetin. The *Rhus verniciflua* stokes extract was filtered, vacuum-concentrated, and then powderized to obtain 0.56 kg of brown dry powder; and the content of fustin in the extract powder that is a final product was 0.01% (w/w); the content of fisetin was 16.7% (w/w); and the content of polyphenol was 56.4% (w/w). That is, the present inventors may obtain the extract, in which all of fustin having low activity was converted into fisetin, an active flavonoid, through a method for preparing a *Rhus verniciflua* stokes extract according to the present invention.

<1-2> Preparation of *Rhus Verniciflua* Stokes Extract Through High Purity Oxygen Bubbling As disclosed in the above Example, <1-1>, 100 l of water was added to 10 kg of *Rhus verniciflua* stokes and then *Rhus verniciflua* stokes was extracted at 95° C. When a large quantity of flavonoid component was included in the extract through 4 hours of the extraction time, high purity oxygen (purity: 95% (v/v)) was bubbled at the bottom of the extractor at the rate of 1.2 l/min using an oxygen cylinder. The time for bubbling was totally 12 hours and the components were analyzed by collecting a sample every hour.

Figure 2:
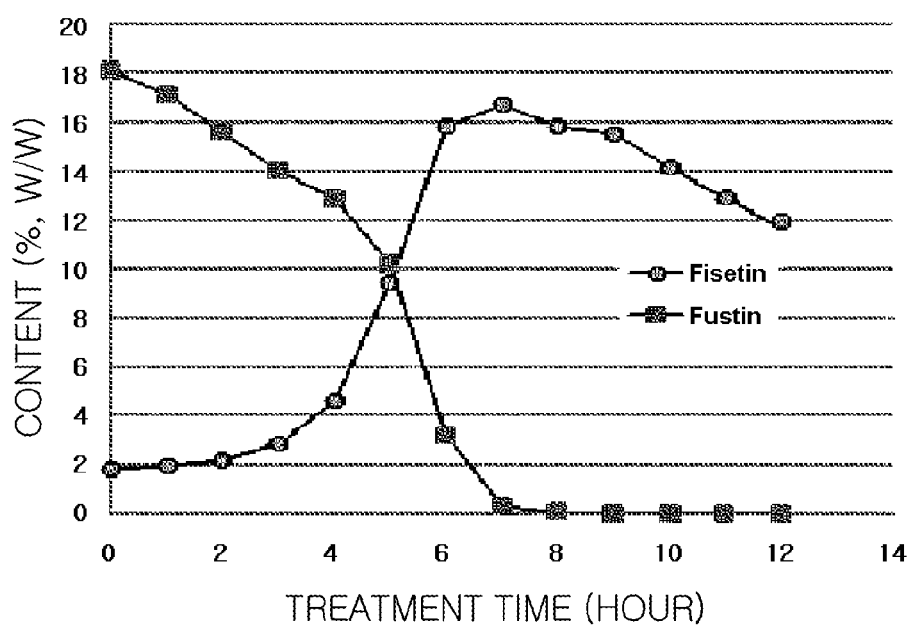
FIG. 2 is a graph showing an effect on converting fustin into fisetin according to time when high purity oxygen bubbling treatment is applied to *Rhus verniciflua* stokes extract.

As a result, the content of fustin was significantly decreased as time passes and the content of fisetin was increased according to the decrease of fustin content (FIG. 2). At 8.8 hours of treatment time, substantially 100% of fustin was converted into fisetin. The rate of converting was rapid and the conversion was completely processed as compared with the use of air. In addition, when the bubbling time is more than necessary, the content of fisetin prepared by converting fustin was slightly reduced so that it can be known that the proper treating time may be important. The extract was filtered, vacuum-concentrated, and then powderized to obtain 0.55 kg of brown dry powder. The content of fustin in the extract powder that is a final product was 0.00% (w/w); the content of fisetin was 12.9% (w/w); and the content of polyphenol was 58.2%.

Comparative Example 1

Preparation of General *Rhus Vernicifula* Stokes Extract 100 l of water was added to 10 kg of *Rhus vernicifula* stokes and then extracted while it was heated at 95° C. for 6 hours. The resulting extract was filtered, vacuum-concentrated, and then powderized to obtain 0.57 kg of brown dry powder. The content of fustin in the extract powder that is a final product was 17.3% (w/w); and the content of fisetin was 1.63% (w/w). The content ratio of fisetin:fustin that were included in *Rhus vernicifula* stokes extract through a method for preparing the conventional *Rhus vernicifula* stokes extract was 1:10.6 and the content of polyphenol was 53.1%. That is, in the case of *Rhus vernicifula* stokes extract through a common method of extracting without a bubbling treatment, the content of fustin was at least 10 times higher than that of the content of fisetin.

Example 2

Preparation of *Rhus Vernicifula Stokes* Extract Using Various Solvents

The *Rhus vernicifula* stokes extracts according to the present invention were prepared by using various extraction solvents. To achieve this, purified water, 50% alcoholic solvent, 80% alcoholic solvent, 80% methanol, and 100% alcoholic solvent were used as an extraction solvent. The conversion rate of fustin into fisetin according to hours during extraction process using each of extraction solvents was investigated and then the times for converting 90% were compared each other. The *Rhus vernicifula* stokes extracts were extracted at 95° C. by adding the extraction solvents that were 10 times to 10 kg of *Rhus vernicifula* stokes as disclosed in the above Example. And then the conversion rate into fisetin was investigated by sampling the extract every hour while bubbling high purity oxygen at the bottom of an extractor in 0.3 VVM (volume/volume/min). The results are shown in the following Table 2.

TABLE 2

Time Required for 90% Conversion of Fustin into Fisetin According to a Type of Solvent.

| | Type of Solvent | | | | |
|---|---|---|---|---|---|
| | Water | 50% Alcoholic Solvent | 80% Alcoholic Solvent | 100% Alcoholic Solvent | 80% Methanol |
| Time required (hrs) | 7.9 | 12.9 | 22.2 | 38.5 | 24.9 |
| Content ratio of Fustin:Fisetin | 0.18 | 0.21 | 0.23 | 0.35 | 0.25 |

As shown in the above Table 2, it has been seen that for the extract prepared by using the method for preparing the *Rhus vernicifula* stokes extract according to the present invention, the fustin in the extract can be converted into fisetin by performing a gas bubbling treatment regardless of a type of used solvents. However, when the content of water in the solvent was decreased, the processing time was increased. Accordingly, from the above result, the present inventors can confirm that the processing time should be controlled in order to increase the conversion rate into fisetin according to a type of solvent in the extraction conditions.

Example 3

Analysis of Anticancer Activity of *Rhus Vernicifula* Stokes Extract According to the Present Invention In order to analyze anticancer activity of the *Rhus vernicifula* stokes extract according to the present invention, firstly the anticancer activities of *Rhus vernicifula* stokes extract prepared by the general method of extracting *Rhus vernicifula* stokes in the above Comparative Example 1, the *Rhus vernicifula* stokes extract according to the present invention prepared from Example <1-1>, and Sample, "A" of Example 6 were mutually compared.

The analysis of anticancer activity were performed by using a comparison of effect on inhibiting a growth of cancer cell after orally administrating the *Rhus vernicifula* stokes extract according to the present invention using a mouse. $5 \times 10^5$ cells of human non-small cell lung cancer cell line, A549, were subcutaneously injected to a nude mouse (Immunodeficient mice (male), CanN. Cg-Foxn1nu/CrljBgi). 7 nude mice were assigned for one group after dividing a control group, the group of Comparative Example 1 and the group of Example <1-1>. The extract was not administrated to the control group, the conventional *Rhus vernicifula* stokes extract extracted from Comparative Example 1 was administrated to the group of Comparative Example 1, and the *Rhus vernicifula* stokes extract according to the present invention extracted in Example <1-1> was administrated to the group of Example <1-1>. 300 mg/kg volume was orally administrated for 24 days. A tumor volume was calculated by using the following formula (A=Long length, B=Short length) after measuring the long length and short length of the tumor using Caliper two times per one week during an administration period; then at 27 days, the tumor was removed and then its weight was measured.

$$V(\text{Tumor Size, mean tumor volume, mm}^3) = \frac{AB^2}{2}$$

As a result, as shown in Table 3, it has been seen that the tumor weight and volume in the mouse of Example <1-1> group were significantly small as compared with the animal model group administrated with the conventional extract. From this, it has been seen that the *Rhus vernicifula* stokes extract according to the present invention has an excellent effect on inhibiting the growth of tumor.

TABLE 3

Comparison of Anticancer Activity of *Rhus vernicifula* Stokes Extract

| | Control Group | <Example 1-1> Group | <Comparative Example 1> Group | Example 6 "A" |
|---|---|---|---|---|
| Tumor Weight | 2 ± 0.4 | 0.75 ± 0.12 | 1.7 ± 0.52 | 0.45 ± 0.12 |

TABLE 3-continued

Comparison of Anticancer Activity of
*Rhus vernicifula* Stokes Extract

| | Control Group | <Example 1-1> Group | <Comparative Example 1> Group | Example 6 "A" |
|---|---|---|---|---|
| (g) Tumor Volume (mm³) | 610 ± 180 | 370 ± 92 | 550 ± 115 | 180 ± 101 |

Example 4

Analysis of Antioxidative Activity of *Rhus Verniciflua* Stokes Extract According to the Present Invention In order to analyze anti-oxidative activity of the *Rhus verniciflua* stokes extract according to the present invention, firstly the anticancer activities of *Rhus verniciflua* stokes extract prepared by the general method of extracting *Rhus verniciflua* stokes in the above Comparative Example 1 and the *Rhus verniciflua* stokes extract according to the present invention prepared from Example <1-1> were mutually compared.

A measurement of anti-oxidative activity was performed by using a method of measuring an electron-donating ability with DPPH method. DPPH is an abbreviation for 1,1-diphenyl-2-picrylhydrazyl, and is widely used a marker for measuring anti-oxidative activity due to its radical. The testing processes were as follows: (1) 2 ml of 0.1 mM DPPH (Sigma, D-9132) dissolved in ethanol was treated to 2 ml of sample dissolved in ethanol; (2) it was mixed for 10 minutes, and then maintained at a dark place for 30 minutes; (3) an absorbance was measured at 520 nm; and (4) the degree of anti-oxidative ability (electron-donating ability, EDA) was calculated. Vitamin E (Fluka, 95420) was used as a positive control group and Formula was as follow.

$$EDA(\text{Electron Donating Ability}) = \frac{(Cabs - Sabs)}{Cabs} \times 100$$

In the above formula, Cabs denotes an absorbance of a negative control group (in the case of treating only ethanol instead of sample) and Sabs denotes an absorbance of sample.

TABLE 4

Comparison of Anti-oxidative Activity
of *Rhus Verniciflua* Stokes Extract

| Sample Name | Anti-oxidative Activity ($IC_{50}$, ug/ml) |
|---|---|
| General *Rhus verniciflua* stokes extract (Comparative Example 1) | 58.9 |
| *Rhus verniciflua* stokes extract according to the present invention (Example 1-1) | 13.3 |
| "A" of Example 6 | 10.5 |
| Pure Fustin | 32 |
| Pure Fisetin | 7.8 |

As a result, as shown in Table 4, it has been seen that the anti-oxidative activity of the *Rhus verniciflua* stokes extract with an enhanced fisetin according to the present invention was at least 4 times excellent as compared with the conventional *Rhus verniciflua* stokes extract. It means that the anti-oxidative activity was significantly improved by converting fustin that is plentifully included in the conventional *Rhus verniciflua* stokes extract into fisetin that is an active flavonoid.

Example 5

Preparation of *Rhus Verniciflua* Stokes Extract Powder with High Content of Fisetin Using Concentration Solution As shown in Example <1-1>, 10 kg of *Rhus verniciflua* stokes was added with 10 times water to extract two times and then concentrated to make 20 l of the concentration solution. Oxygen gas was bubbled at 0.4 VVM for 12 hours, and then the prepared *Rhus verniciflua* stokes extract was concentrated to obtain 470 g of *Rhus verniciflua* stokes extract powder, in which the content of fustin was 1.2% (w/w) and the content of fisetin was 15.8% (w/w). At this time, the content ratio of fisetin:fustin was 1:0.076.

Example 6

Preparation of Solvent Fraction with High Content of Fisetin

Each 100 g of the extracts obtained from the above Example <1-1> and Comparative Example 1 was dissolved in 5,000 ml of water; 7,500 ml of ethyl acetate was added; then it was intensely mixed for 10 minutes using a mixer; and then it was maintained at room temperature for separating a layer. An upper layer of ethyl acetate was collected; then the solvent was removed; and then components were analyzed. As a result, the content of fisetin was 42.5% (w/w) in the case of Example <1-1> sample (referred to "A") and the content of fisetin was 7.5% (w/w) in the case of Comparative Example 1 sample (referred to "B").

Example 7

Preparation of Fisetin Crystalline 10 g of the solid obtained from the above Example 6 was dissolved in 50 ml of ethanol; and then poured into cold water (cold storage) at once. At this time, yellow crystalline of fisetin was weakly produced at the same time. It was centrifuged at 3,000 rpm for 20 minutes to recover. The crystalline obtained by this example was dried and then its purity was analyzed with HPLC. As a result, the content of water was 2.8% (w/w) and the purity of fisetin was 96.5% (w/w).

A method for preparing a *Rhus verniciflua* stokes extract according to the present invention can provide *Rhus verniciflua* stokes extract having high content of fisetin by converting fustin into fisetin through a gas bubbling treatment to the conventional *Rhus verniciflua* stokes extract including low content of fisetin and high content of fustin. Accordingly, the *Rhus verniciflua* stokes extract having a large quantity of fisetin according to the present invention can be commercialized as anticancer drugs, anticancer foods, foods for preventing cancer, health functional foods, and the like due to its excellent bioactivity. In addition, the developments of the related industries can be induced due to a high added-value of

*Rhus verniciflua* stokes. Also, a method of converting fustin into fisetin according to the present invention can be used as a method of increasing the content of a high active flavonoid by applying to other natural substances thereby becoming the base technology for leading high functionalization of natural substances.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A composition for treating cancer consisting essentially of therapeutically effective amounts of a *Rhus verniciflua* stokes extract, a solvent selected from the group consisting of water, ethanol, acetone, ethyl acetate, n-butanol, and chloroform, and a mixture thereof, and an excipient selected from the group consisting of lactose, dextrose, sucrose, sorbitol, mannitol, xylitol, erythritol, maltitol, acacia, alginate, gelatin, calcium phosphate, calcium silicate, cellulose, methylcellulose, polyvinylpyrrolidone, methyl hydroxybenzoate, propyl hydroxybenzoate, talc and magnesium stearate, and a mixture thereof.

2. The composition of claim 1, wherein the *Rhus verniciflua* extract has the compounds fisetin, fustin or mixtures thereof in it.

3. The composition of claim 2, wherein the ratio of fisetin:fustin is about 1:0 to about 2:1.

4. The composition of claim 2, wherein the concentration of fusetin is about 30 to 45% (w/w).

* * * * *